United States Patent
Itoh et al.

(10) Patent No.: US 7,800,053 B2
(45) Date of Patent: Sep. 21, 2010

(54) METHOD OF EVALUATING ION IRRADIATION EFFECT, PROCESS SIMULATOR AND DEVICE SIMULATOR

(75) Inventors: Kohei Itoh, Yokohama (JP); Yasuo Shimizu, Yokohama (JP)

(73) Assignee: Keio University, Tokyo (JP)

( * ) Notice: Subject to any disclaimer, the term of this patent is extended or adjusted under 35 U.S.C. 154(b) by 275 days.

(21) Appl. No.: 11/723,245

(22) Filed: Mar. 19, 2007

(65) Prior Publication Data

US 2007/0267572 A1  Nov. 22, 2007

(30) Foreign Application Priority Data

May 17, 2006  (JP) .............................. 2006-137251

(51) Int. Cl.
  *H01L 29/15* (2006.01)
(52) U.S. Cl. .................... 250/282; 250/281; 250/492.1; 250/492.2; 250/492.21; 438/5; 438/14; 438/795; 438/798
(58) Field of Classification Search ................. 250/281, 250/282, 492.1, 492.2, 492.21, 492.3, 396 R, 250/399, 306, 307, 309; 438/14, 16, 5, 7, 438/795, 797, 798; 257/E21.021, E23.041, 257/E23.134, E23.173, E27.001
See application file for complete search history.

(56) References Cited

U.S. PATENT DOCUMENTS

| | | | | |
|---|---|---|---|---|
| 4,935,194 A * | 6/1990 | Verschoore | .................. | 376/108 |
| 5,303,319 A * | 4/1994 | Ford et al. | .................... | 385/131 |
| 5,350,919 A * | 9/1994 | Hirano et al. | ................ | 250/282 |
| 5,521,377 A * | 5/1996 | Kataoka et al. | .......... | 250/252.1 |
| 5,637,511 A * | 6/1997 | Kurihara | ....................... | 438/79 |
| 5,804,981 A * | 9/1998 | Lowell et al. | ................ | 324/752 |
| 5,917,195 A * | 6/1999 | Brown | .......................... | 257/22 |
| 5,947,053 A * | 9/1999 | Burnham et al. | ............ | 116/208 |
| 6,054,333 A * | 4/2000 | Bensaoula | ...................... | 438/9 |
| 6,078,045 A * | 6/2000 | Maul et al. | ..................... | 850/43 |
| 6,235,617 B1* | 5/2001 | Kawai | .......................... | 438/520 |
| 6,608,315 B1* | 8/2003 | Saadatmand et al. | ... | 250/492.21 |
| 6,677,168 B1* | 1/2004 | Zhao et al. | ..................... | 438/14 |
| 7,247,546 B2* | 7/2007 | Bedell et al. | ................. | 438/478 |
| 7,494,725 B2* | 2/2009 | Maeda et al. | ............. | 428/831 |
| 2003/0008404 A1* | 1/2003 | Tomita et al. | .................. | 436/72 |
| 2003/0131787 A1* | 7/2003 | Linares et al. | ................ | 117/93 |
| 2003/0186519 A1* | 10/2003 | Downey et al. | ............. | 438/530 |
| 2004/0080050 A1* | 4/2004 | McMillin et al. | ............ | 257/758 |
| 2004/0115343 A1* | 6/2004 | Carcia et al. | ................. | 427/160 |

(Continued)

FOREIGN PATENT DOCUMENTS

JP                63030290 A  *  2/1988

(Continued)

*Primary Examiner*—Bernard E Souw
*Assistant Examiner*—Michael J Logie
(74) *Attorney, Agent, or Firm*—Westerman, Hattori, Daniels & Adrian, LLP

(57) ABSTRACT

Provided are a method of evaluating an ion irradiation effect, a process simulator and a device simulator, which allow the influence of ion irradiation on atoms making up a substrate to be evaluated with high accuracy. The method includes irradiating a sample with a beam of ions, and evaluating influence of the ions used for the irradiation on atoms making up the sample, provided that the sample is prepared by alternately and periodically stacking a plurality of thin film layers, and of the plurality of thin film layers, the layer of at least one kind is composed of an isotope layer.

9 Claims, 14 Drawing Sheets

U.S. PATENT DOCUMENTS

| | | | |
|---|---|---|---|
| 2004/0169225 A1* | 9/2004 | Burden | 257/347 |
| 2004/0241460 A1* | 12/2004 | Bedell et al. | 428/446 |
| 2005/0230615 A1* | 10/2005 | Furutani et al. | 250/287 |
| 2006/0027808 A1* | 2/2006 | Bedell et al. | 257/65 |
| 2006/0221474 A1* | 10/2006 | Imai et al. | 359/883 |
| 2006/0255296 A1* | 11/2006 | Borden | 250/492.21 |
| 2006/0278611 A1* | 12/2006 | Sato et al. | 216/66 |

FOREIGN PATENT DOCUMENTS

| | | | |
|---|---|---|---|
| JP | 6-273289 A | | 9/1994 |
| JP | 10340861 A | * | 12/1998 |
| JP | 11297624 A | * | 10/1999 |
| JP | 2000260974 A | * | 9/2000 |
| JP | 2004-79656 A | | 3/2004 |

\* cited by examiner

FIG 13
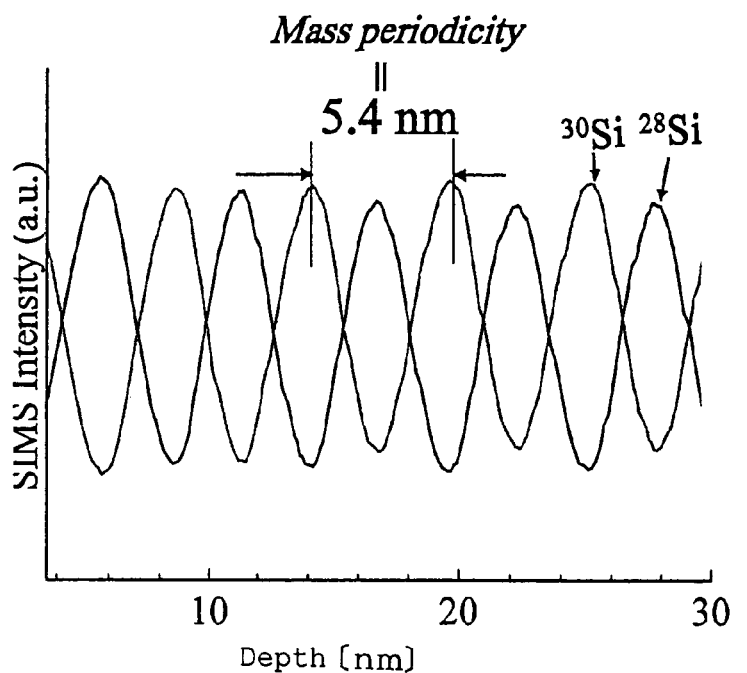
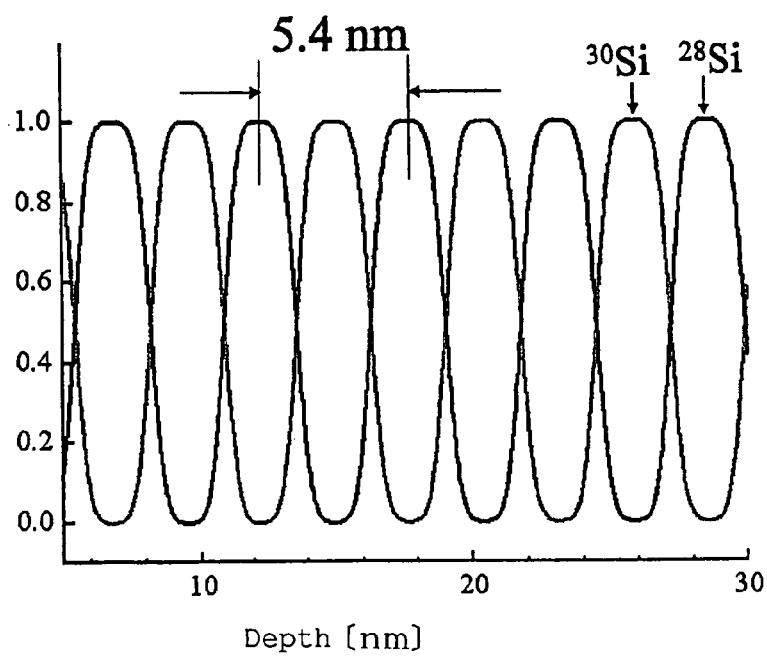

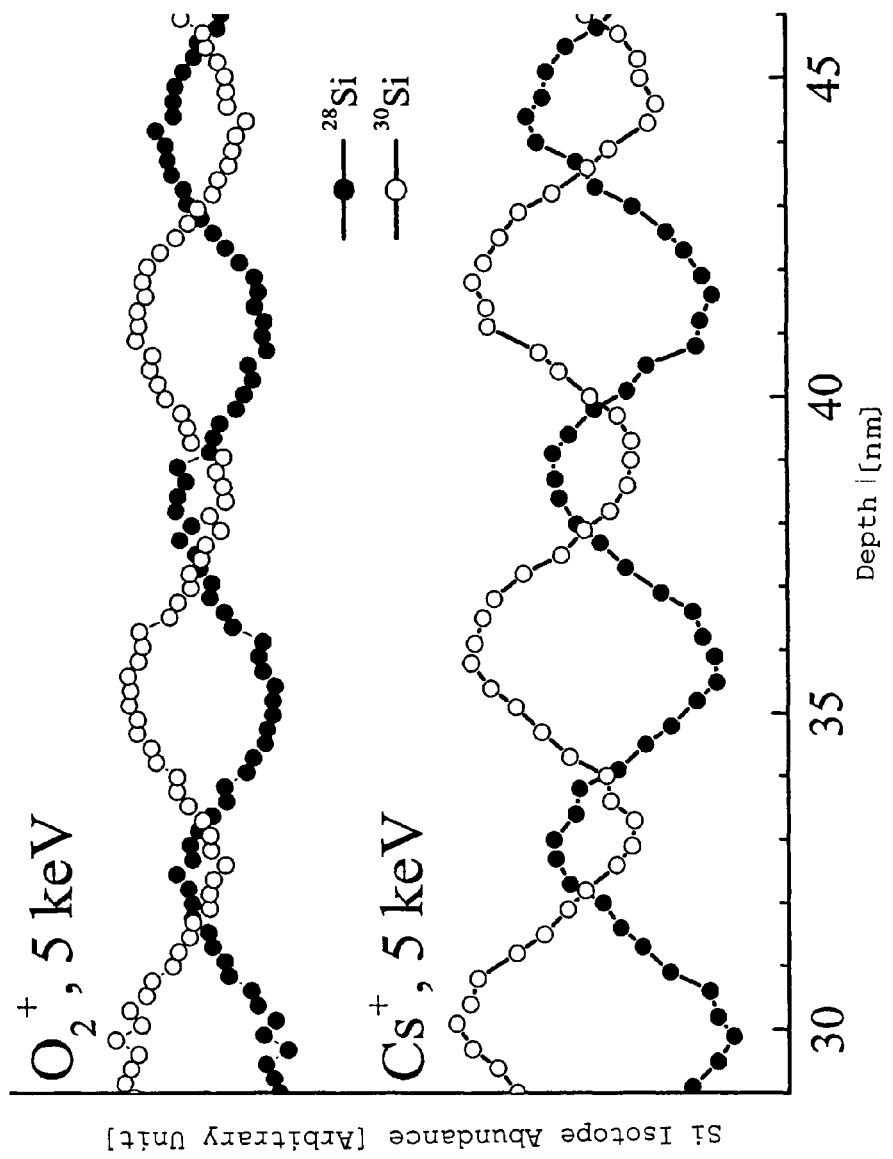

METHOD OF EVALUATING ION IRRADIATION EFFECT, PROCESS SIMULATOR AND DEVICE SIMULATOR

BACKGROUND OF THE INVENTION

1. Field of the Invention

The present invention relates to a method of evaluating an ion irradiation effect, a process simulator and a device simulator. More specifically, it relates to a method of evaluating an ion irradiation effect, which is distinctive in an arrangement for evaluating the effect of ion irradiation in ion implantation or ion etching with high accuracy, a process simulator and device simulator.

2. Description of the Related Art

The ion implantation technique has been used as a method of forming an impurity-doped region in a semiconductor device for a step of forming a source and a drain of a MOSFET, etc. Various simulation methods have been proposed for the purpose of estimating an impurity distribution resulting from ion implantation like this with high accuracy in advance (see e.g. JP-A-2004-079656).

There are various kinds of parameters for performing such simulation, which require numerical values measured in fact. For example, the distribution of an actual impurity concentration after ion implantation has been measured in reality by use of e.g. SIMS (Secondary Ion Mass Spectrometry) or the like.

In the case where SIMS is used to perform composition analysis of a thin film, etc., a standard sample composed of different materials alternately stacked into a multilayered form is used to calibrate the resolution of a direction of the depth, and the calibration is performed based on an ion intensity distribution of the standard sample.

However, some standard samples like this have a problem that because of having two or more layers of different materials, the samples have a so-called interface effect developed in the vicinity of an interface between the layers of different materials, which can expand or shrink an ion intensity distribution extraordinarily.

Hence, it has been proposed to use a standard sample which has alternately-stacked atomic layers of different isotopes, but common in element species (see e.g. JP-A-06-273289).

As for an isotope standard sample like this, isotopes are slightly different in atomic mass number, but entirely identical in chemical property. Therefore it has been reported that the interface effect and matrix effect disappear, and the resolution in a direction of the depth can be improved in accuracy.

On the other hand, a silicon (Si) substrate is damaged by ion implantation, and therefore the evaluation of such damage has been made by use of a channeling method in Rutherford backscattering spectrometry or a transmission electron microscope (see e.g. Journal of Applied Physics, Vol. 88, p. 3993, 2000).

Likewise, such damage will be caused in nanometer-scale ion beam machining by means of FIB (Focused Ion Beam) technique.

However, a conventional method of evaluating a damage has had a problem that it is difficult to quantitatively know the extent to which the silicon atoms in a portion damaged by ion irradiation are displaced.

Further, in the case of analysis by SIMS, a sample is analyzed while being etched by ions. Therefore, there has been a problem that it is difficult to evaluate what influences an effect by a physical force caused by ion etching, e.g. ion beam induced diffusion has on a composition distribution and a silicon lattice.

Therefore, the invention aims at evaluating an influence which ion irradiation exerts on atoms constituting a substrate with high accuracy.

SUMMARY OF THE INVENTION

A means for resolving the problems in association with the invention will be described with reference to FIG. 1 which is a view of assistance in explaining an arrangement according to the invention in theory.

The reference numeral 2 in the drawing represents a substrate such as a monocrystalline Si substrate.

Making a reference to FIG. 1 helps understand the means for resolving the problems.

Means 1

To resolve the above problems, the invention offers a method of evaluating an ion irradiation effect which is characterized by the following steps. The first is irradiating a sample 1 prepared by alternately and periodically stacking a plurality of thin film layers with a beam of ions 5. The second is evaluating influence of the ions 5 used for the irradiation on atoms making up the sample 1. In the method, of the plurality of thin film layers, the layer of at least one kind is composed of an isotope layer 3.

As stated above, when a sample 1 including periodically arranged isotope layers 3 is used, it becomes possible to evaluate influence of ions 5 used for the irradiation on atoms making up the sample 1 based on distributions of isotopes, i.e. depth profiles of isotopes, with high accuracy.

Incidentally, the above patent document JP-A-6-273289 merely proposes a standard sample 1 for increasing the resolution of SIMS in a direction of the depth, and does not describe that some treatment is performed on the standard sample 1, and the displacement of constituent atoms of the sample owing to the treatment is evaluated based on the changes in distributions of isotopes.

Means 2

Also, the method of evaluating an ion irradiation effect according to the invention stated in MEANS 1 is characterized in that the sample 1 includes two kinds of isotope layers 3 and 4.

Use of the sample 1 including two kinds of isotope layers 3 and 4 as stated above enables influence of ion irradiation on atoms making up the sample 1 to be evaluated with high accuracy.

Incidentally, a typical example of the two kinds of isotope layers 3, 4 in this case is a combination of a $^{28}$Si layer and a $^{30}$Si layer.

Means 3

Further, the method of evaluating an ion irradiation effect according to the invention stated in MEANS 1 is characterized in that the sample 1 is a sample which is prepared by alternately and periodically stacking two kinds of thin film layers, provided that the two kinds of thin film layers consist of a thin film layer of one kind composed of a layer having a natural composition ratio and a thin film layer of the other kind composed of an isotope layer 3.

In the case where the thin film layer of one kind is an isotope layer 3 like this, the thin film layer of the other kind may be a layer having a natural composition ratio, which enables the reduction in the manufacturing cost of the sample 1.

Incidentally, a typical example of the two kinds of thin film layers in this case is a combination of a Si layer having a natural composition ratio and a $^{28}$Si layer.

Means 4

Still further, the method of evaluating an ion irradiation effect according to the invention stated in any one of MEANS 1 to 3 is characterized in that the step of ion irradiation is one of an ion implantation step and an ion etching step, and influence of ions 5 in the ion beam used for the irradiation on atoms making up the sample 1 is evaluated by means of secondary ion mass spectrometry.

As stated above, typical examples of the step of ion irradiation targeted for evaluation are an ion implantation step and an ion etching step. Evaluation of their influences by means of the secondary ion mass spectrometry can realize evaluation of such influences by a relatively untroublesome means for measurement.

As the secondary ion mass spectrometry per se carries ion etching, evaluation can be made with higher accuracy when the influence thereof is taken into account.

Means 5

Also, the invention offers a process simulator characterized in that characteristic values derived from evaluation according to the method of evaluating an ion irradiation effect of any one of MEANS 1 to 4 are stored as parameters in the process simulator.

As stated above, when the characteristic values derived from evaluation according to the above-described method of evaluating an ion irradiation effect are stored in the process simulator as parameters, a highly accurate process simulation taking into account the displacement of atoms resulting from the damage caused by ions, which has been unable to be evaluated conventionally, can be achieved.

Means 6

In addition, the invention offers a device simulator characterized in that characteristic values derived from evaluation according to the method of evaluating an ion irradiation effect of any one of MEANS 1 to 4 are stored in the device simulator as parameters.

As stated above, when the characteristic values derived from evaluation according to the above-described method of evaluating an ion irradiation effect are stored in the device simulator as parameters, a highly accurate device simulation taking into account the displacement of constituent atoms of a substrate resulting from the damage caused by ions, which has been unable to be evaluated conventionally, can be achieved. Particularly, in regard to a device having a hetero interface, e.g. the change in the mobility of a carrier owing to mixing of constituent atoms of a substrate can be evaluated with high accuracy.

According to the invention, it is made possible by using a sample having isotope atoms arranged regularly and measuring the change in depth profiles of the isotope atoms to simulate damages caused by ions including the displacement of constituent atoms with high accuracy, which have been unable to be evaluated conventionally.

Therefore, according to a method of evaluating an ion irradiation effect that the invention provides, a sample prepared by alternately and periodically stacking a plurality of thin film layers, of which a thin film layer of at least one kind is composed of an isotope layer, or typically a $^{28}Si_n/^{30}Si_n$ sample (n represents the number of atomic layers constituting each layer) is irradiated with ions, followed by performing ion implantation or ion etching on the sample typically. Then, the influence of ions used for the irradiation on atoms constituting the sample is evaluated by e.g. the secondary ion mass spectrometry.

With a process simulator that the invention offers, characteristic values derived from evaluation according to the above-described method of evaluating an ion irradiation effect, e.g. values derived from evaluation of standard deviations of recoils of silicon atoms owing to ion irradiation are taken in the process simulator as parameters, whereby it becomes possible to quantitatively evaluate mixing of silicon atoms caused by ion irradiation and a thermal treatment after that.

Further, with a device simulator that the invention offers, characteristic values derived from evaluation according to the above-described method of evaluating an ion irradiation effect, e.g. values derived from evaluation of standard deviations of recoils of Ga, Al and In atoms in the vicinity of a hetero interface owing to ion irradiation are taken in the device simulator as parameters, whereby it becomes possible to quantitatively evaluate e.g. the change in the mobility of a carrier owing to mixing of constituent atoms of a substrate caused by ion irradiation and a thermal treatment after that.

BRIEF DESCRIPTION OF THE DRAWINGS

FIG. 13 is a view for comparison of sample evaluation between SIMS and Raman scattering;

FIG. 15 is a view of assistance in explaining the dependence of substrate damage on an ion species used for irradiation.

DESCRIPTION OF THE PREFERRED EMBODIMENTS

First Embodiment

A method of evaluating mixing caused by ion implantation according to the first embodiment of the invention will be described here with referring now to FIGS. 2 to 11.

Figure 1:
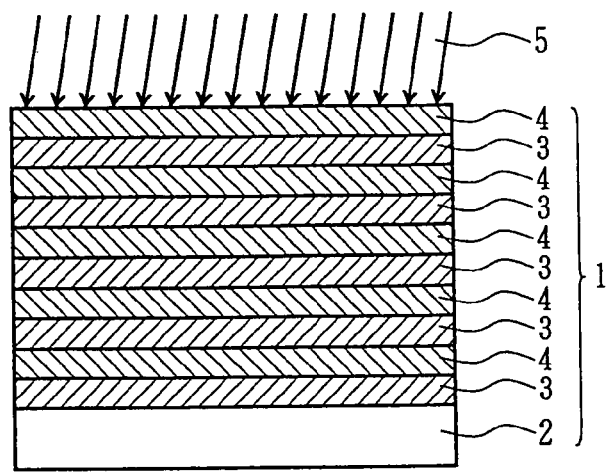
FIG. 1 is a view of assistance in explaining an arrangement according to the invention in theory.
Figure 2:
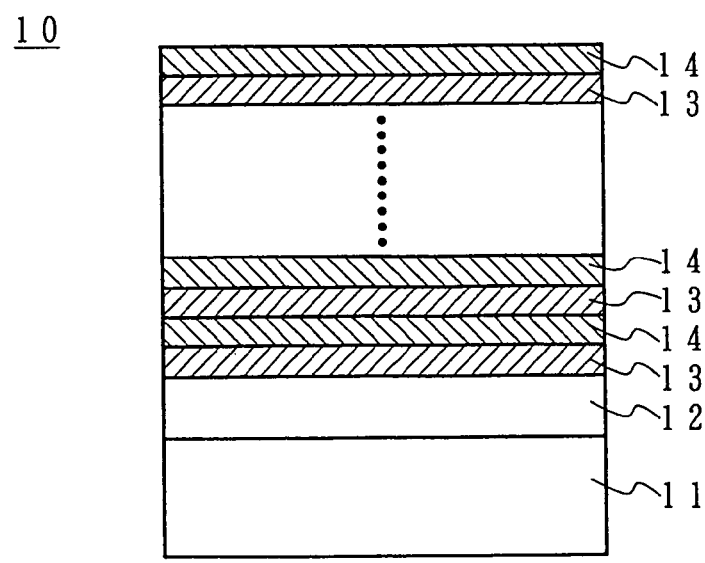
FIG. 2 is a schematic sectional view of a sample used in a method of evaluating mixing caused by ion implantation according to the first embodiment of the invention.

Referring to FIG. 2, there is presented a schematic sectional view of a sample used in the method of evaluating mixing caused by ion implantation according to the first embodiment of the invention. On a Si buffer layer 12 of a natural composition ratio on a monocrystalline Si substrate 11 having a natural composition ratio with its (001) plane made a top surface, $^{30}Si_{20}$ layers 13 each composed of twenty atomic layers and $^{28}Si_{20}$ layers 14 each composed of twenty atomic layers are alternately stacked to e.g. fifteen cycles of the layers by means of molecular beam epitaxy.

In this case, the thickness of one atomic layer of each Si layer is about 0.136 nm, and therefore the thickness of one cycle of $^{28}Si_{20}/^{30}Si_{20}$ is 5.4 nm approximately.

Incidentally, the abundances of silicon isotopes are as follows.
$^{28}Si$: 92.2%
$^{29}Si$: 4.7%
$^{30}Si$: 3.1%

However, for the purpose of making larger the mass ratio of isotopes, the isotopes, $^{28}Si$ and $^{30}Si$ are selected here.

Figure 3:
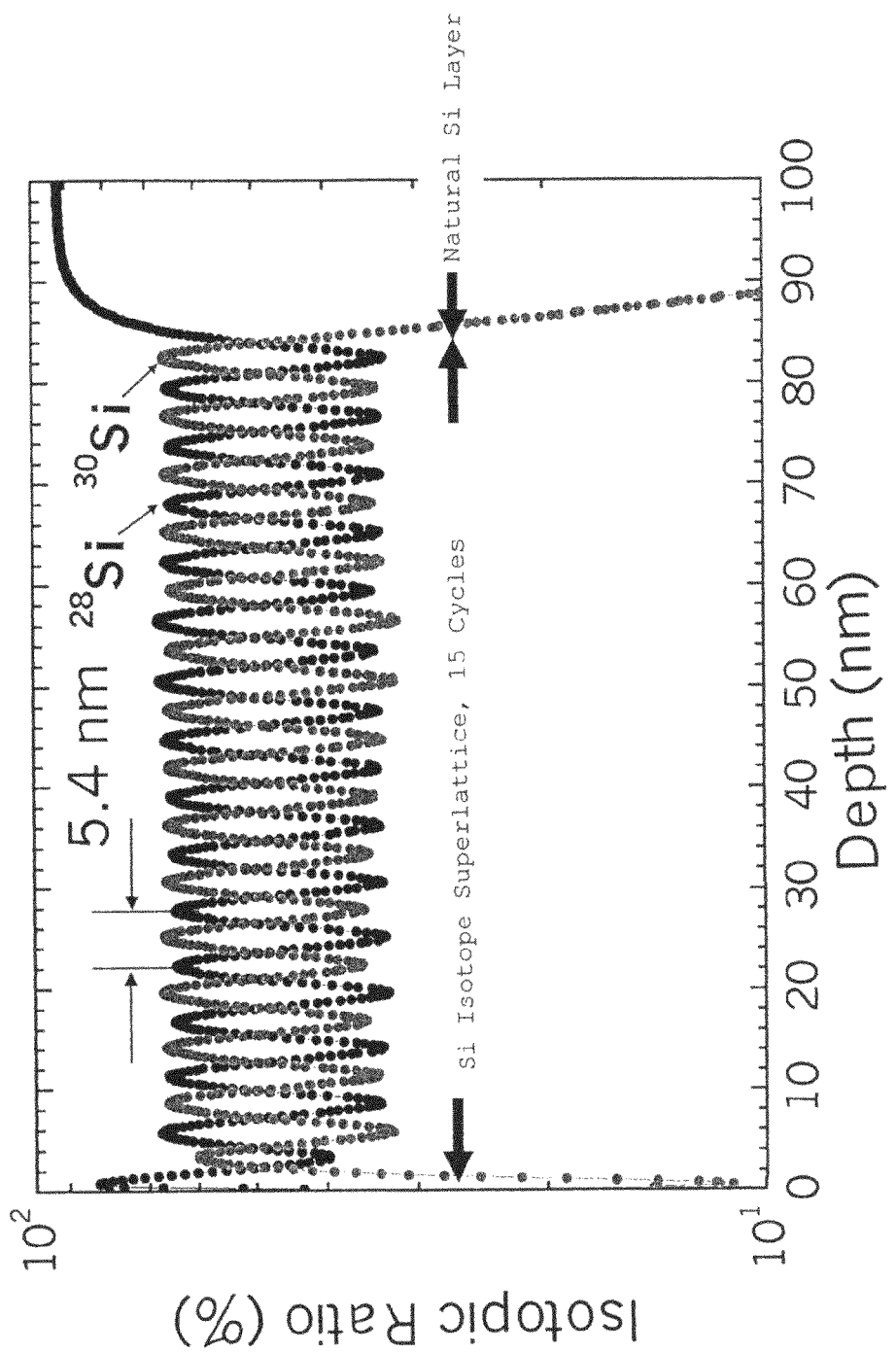
FIG. 3 is a view showing SIMS depth profiles of Si isotopes in a sample.

Referring to FIG. 3, there is presented a view showing SIMS depth profiles of Si isotopes in the sample. It can be seen from the drawing that $^{30}Si$ and $^{28}Si$ are alternately distributed with a cycle of about 5.4 nm.

Now, it is noted that in this SIMS analysis, secondary ions are analyzed while Cs+ ion is applied to the sample with an acceleration energy of 1 keV and an incident angle of 45 degrees, and individual abundances of the isotope ratio are normalized with respect to those of Si buffer layer 12 of the natural composition ratio. The conditions also apply to the cases stated below.

Figure 4:
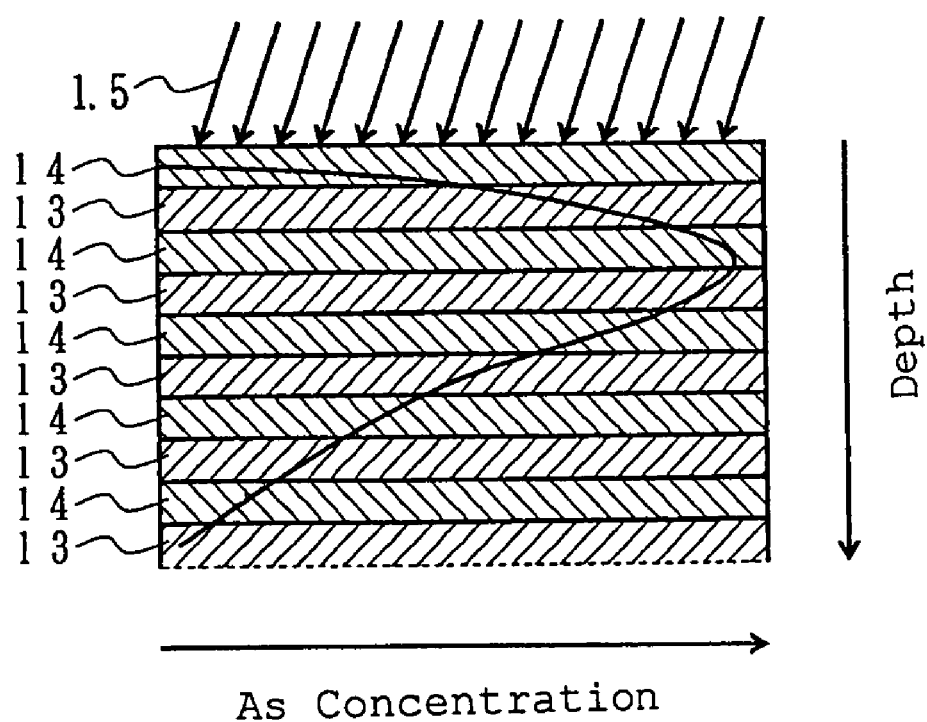
FIG. 4 is a view of assistance in explaining the distribution of an arsenic (As) concentration after ion implantation.

Referring to FIG. 4, there is presented a view of assistance in explaining the distribution of an arsenic (As) concentration after ion implantation. As ions ($^{75}As$) 15 are implanted into the sample 10 with an acceleration energy of e.g. 25 keV and a dose systematically changed within a range of $10^{13}$ to $10^{15}$ cm$^{-2}$. In this case, the distribution of implanted As ions 15 has a peak at a position of about 20 nm from the surface.

Figure 5:
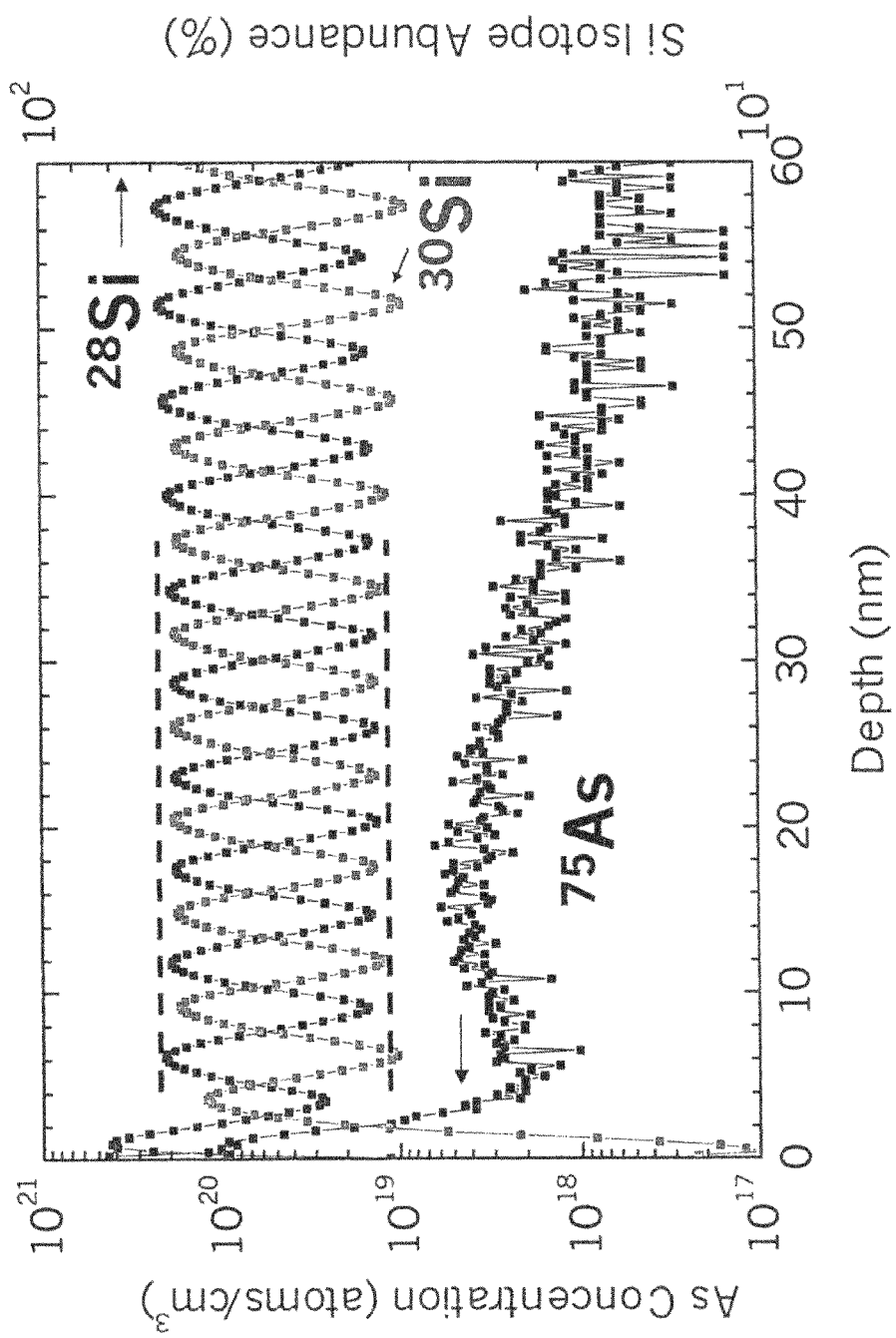
FIG. 5 is a view showing SIMS depth profiles of Si isotopes in the sample after implantation of As ions ($10^{13}$ cm$^{-2}$)

Referring to FIG. 5, there is presented a view showing SIMS depth profiles of Si isotopes in the sample after implantation of As ions ($10^{13}$ cm$^{-2}$). Although some disorder arises at and in the vicinity of the surface, $^{30}Si$ and $^{28}Si$ are distributed regularly and alternately at a position below a depth of 5.4 nm from the surface. It can be seen that little mixing is caused under the condition of a dose of about $10^{13}$ cm$^{-2}$.

Now, samples used for this SIMS analysis are unannealed ones, and this condition applies to the cases stated below.

Figure 6:
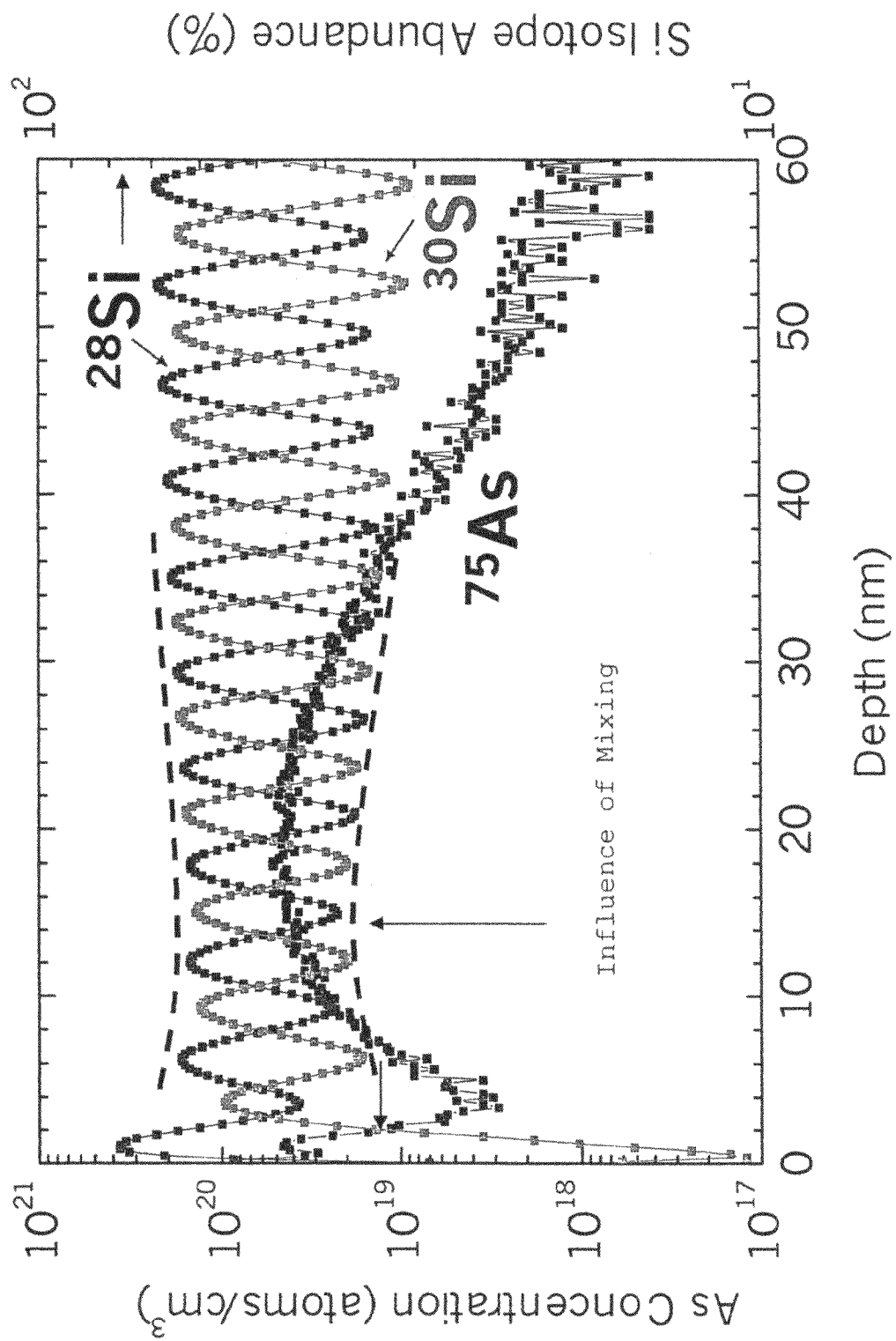
FIG. 6 is a view showing SIMS depth profiles of Si isotopes in the sample after implantation of As ions ($10^{14}$ cm$^{-2}$)

Referring to FIG. 6, there is presented a view showing SIMS depth profiles of Si isotopes in the sample after implantation of As ions ($10^{14}$ cm$^{-2}$). In addition to some disorder arising at and in the vicinity of the surface, both $^{30}Si$ and $^{28}Si$ abundances are made smaller to a depth of about 40 nm from the surface. Therefore, it can be seen that mixing is caused.

Figure 7:
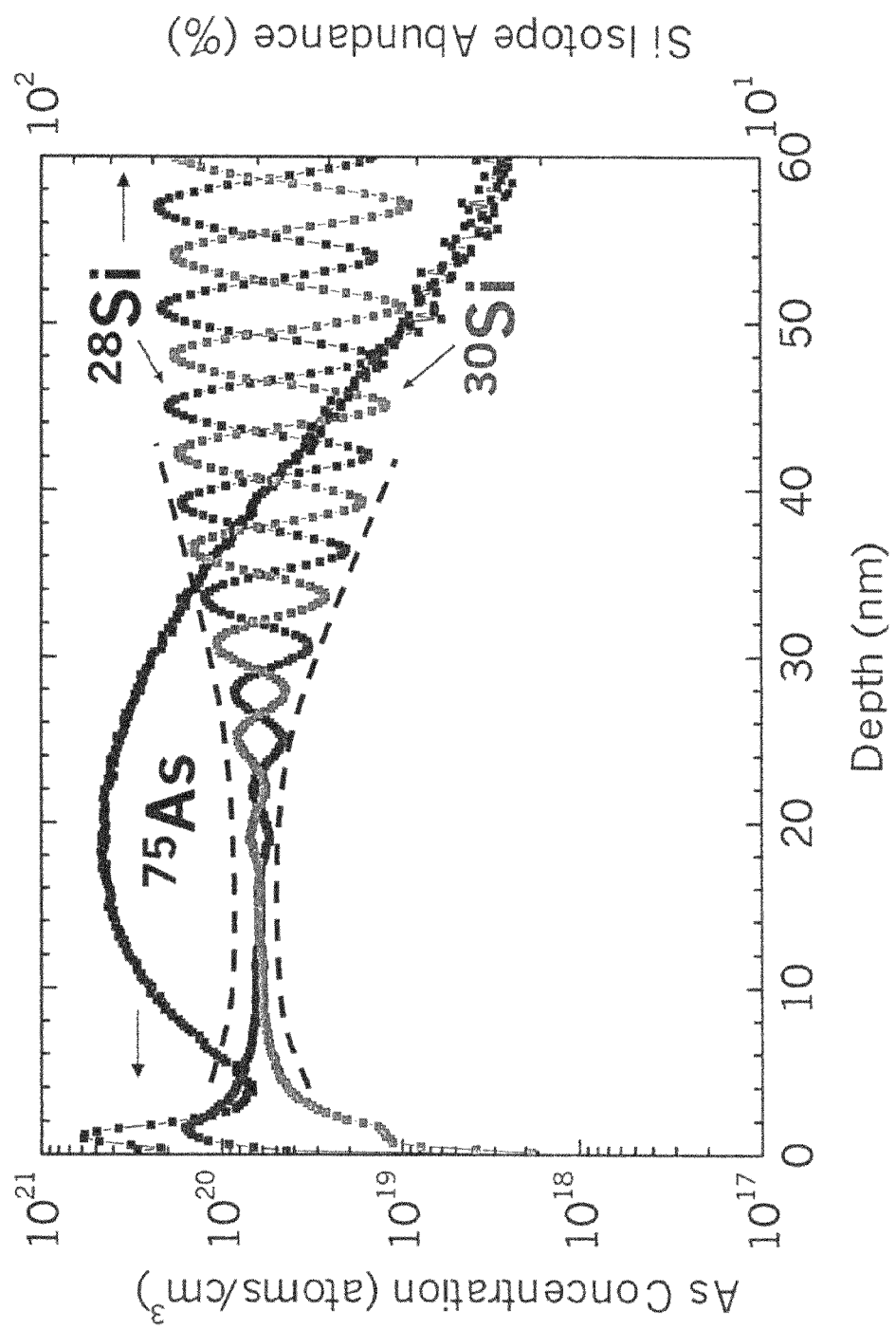
FIG. 7 is a view showing SIMS depth profiles of Si isotopes in the sample after implantation of As ions ($10^{15}$ cm$^{-2}$)

Referring to FIG. 7, there is presented a view showing SIMS depth profiles of Si isotopes in the sample after implantation of As ions ($10^{15}$ cm$^{-2}$). It can be seen that the periodicities of $^{30}Si$ and $^{28}Si$ disappear completely to a depth of about 20 nm from the surface.

Figure 8:
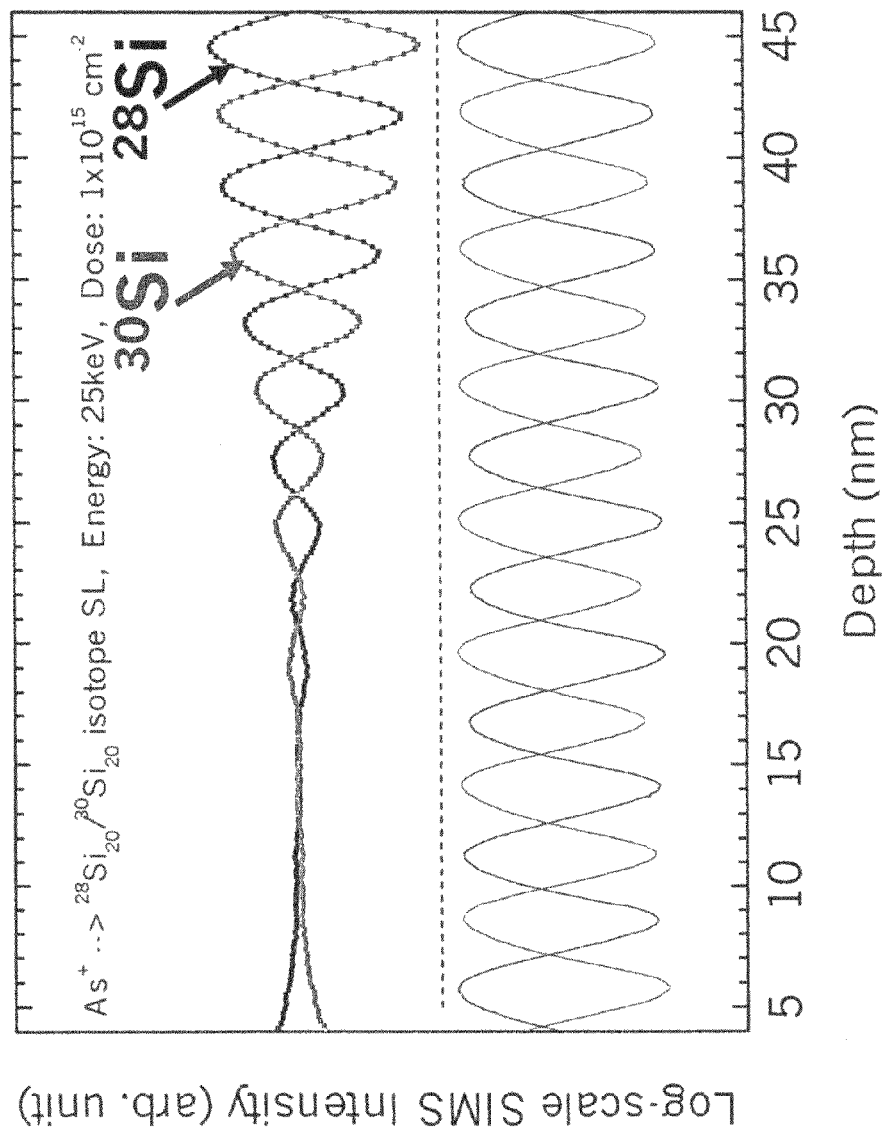
FIG. 8 is a view of assistance in comparing distributions of $^{28}Si$ and $^{30}Si$ concentrations before and after implantation of As ions.

Referring to FIG. 8, there is presented a view of assistance in comparing distributions of $^{28}Si$ and $^{30}Si$ concentrations before and after implantation of As ions. In the drawing, the data shown in FIGS. 3 and 7 are compared within a depth range of 4 to 46 nm from the surface.

Figure 9:
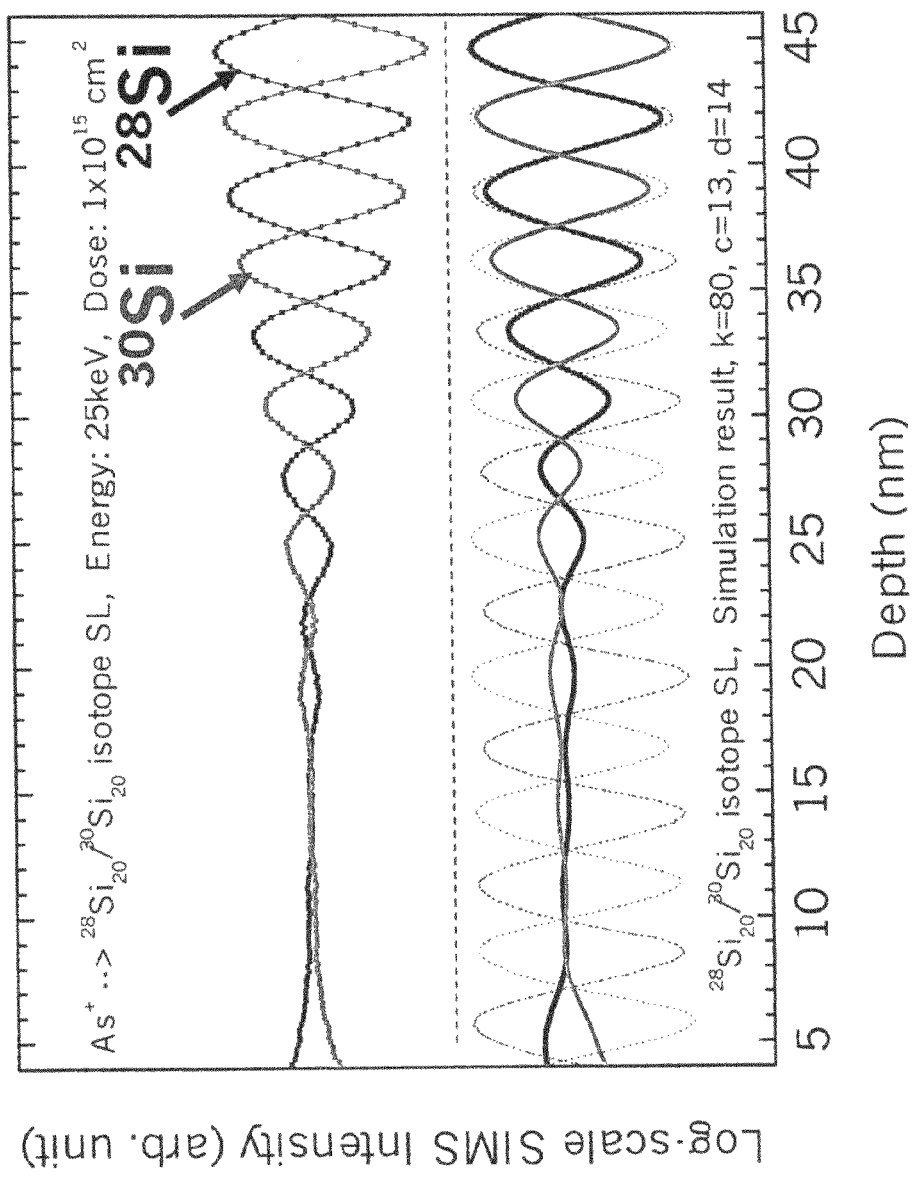
FIG. 9 is a view of assistance in comparing the results of an experiment and a simulation concerning distributions of $^{28}Si$ and $^{30}Si$ concentrations after implantation of As ions.

Referring to FIG. 9, there is presented a view of assistance in comparing the results of an experiment and a simulation concerning distributions of $^{28}Si$ and $^{30}Si$ concentrations after implantation of As ions. The result of simulation is overlaid on FIG. 3 and shown in the lower portion of the drawing.

An equation to draw the result of simulation in this case is given by the following expression (1), by which the displacement of atoms damaged by ion implantation can be evaluated by recreating the distribution $C_{as-impla}(x)$ of the concentration of each isotope after ion implantation by use of the convolution integral of the distribution $C_{as-grown}(x)$ of the concentration before ion implantation, provided that x represents a depth from the surface:

$$C_{as-impla}(x) = INT\{C_{as-grown}(x') \times [1/((2\pi)^{1/2} \times \sigma)] \times \exp[-(x-x')^2/2\sigma^2]dx'\} \ [x' = -\infty \to +\infty] \quad (1),$$

$$\text{where } \sigma(x) = k/[(2\pi)^{1/2} \times c] \times \exp[-(x-d)^2/2c^2] \quad (2).$$

As a matter of convenience of preparation of the specification, $INT\{A(x')dx'=\} \ [x'=-\infty \to +\infty]$ means that the function $A(x')$ placed between a pair of braces is integrated with respect to x' from $-\infty$ to $+\infty$.

Further, k, c and d are fitting parameters, and they are set in order to fit the simulation result to the experimental result plotted in the upper portion of the drawing as follow: k=80, c=13, and d=14.

Figure 10:
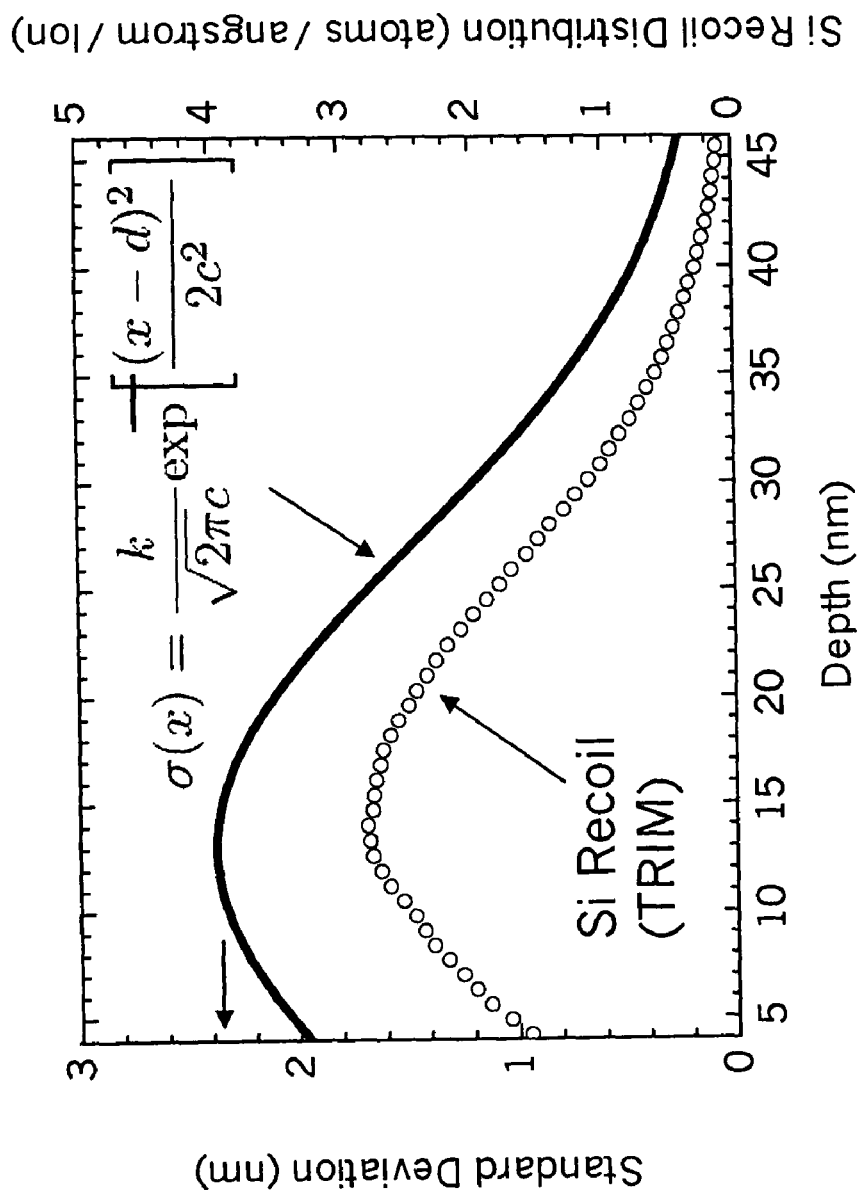
FIG. 10 is a view of assistance in comparing the standard deviations σ(x) for the experimental result and a depth profile of recoil silicon atoms obtained from calculation by TRIM.

Referring to FIG. 10, there is presented a view of assistance in comparing the standard deviations $\sigma(x)$ for the experimental result and a depth profile of recoil silicon atoms obtained from calculation by TRIM. The experimental result was obtained under the condition where the sample had been subjected to sheer ion implantation only without undergoing thermal treatment (i.e. annealing). Accordingly, in this case, the experimental result should match up to the result offered by a standard simulator [TRIM] which shows that ion irradiation causes silicon atoms of the substrate to be removed from lattice positions. In fact, FIG. 10 shows a good correlation between the results.

Thus, mixing of silicon atoms can be evaluated quantitatively based on the changes in intensities of Si isotopes obtained with SIMS.

Further, the distribution of displacement of Si after thermal treatment, which TRIM cannot offer, can be obtained because the structure is heated, and k, c and d are derived from fitting.

FIG. 9 shows the case where the dose is $10^{15}$ cm$^{-2}$. However, the dependence of the degree of mixing on doses can be grasped quantitatively by simulating the degrees of mixing in cases of various doses and fitting the fitting parameters k, c and d to values which enable an experimental result to be recreated faithfully.

Figure 11:
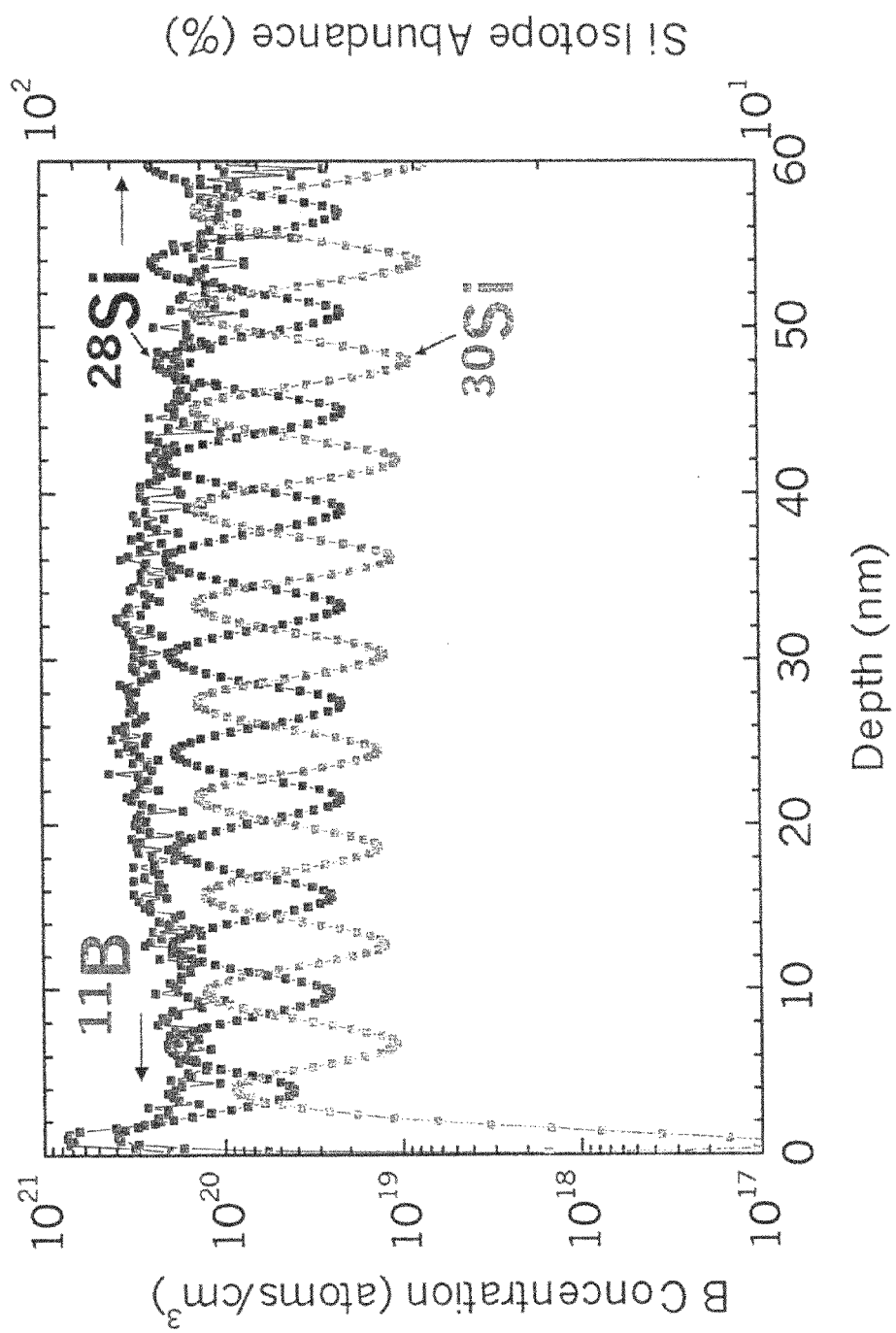
FIG. 11 is a view showing SIMS depth profiles of Si isotopes in the sample after implantation of boron (B) ions ($10^{15}$ cm$^{-2}$)

Referring to FIG. 11, there is presented a view showing SIMS depth profiles of Si isotopes in the sample after implantation of B ions ($10^{15}$ cm$^{-2}$). It can be seen that less mixing is caused in comparison to As ions.

In this case, the abundance of $^{28}Si$ higher than that of $^{30}Si$ in each periodic structure is not ascribable to the mixing, and it can be inferred that such relation of the isotope abundances results from the step of normalization with respect to the Si buffer layer 12 having the natural composition ratio.

Figure 12:
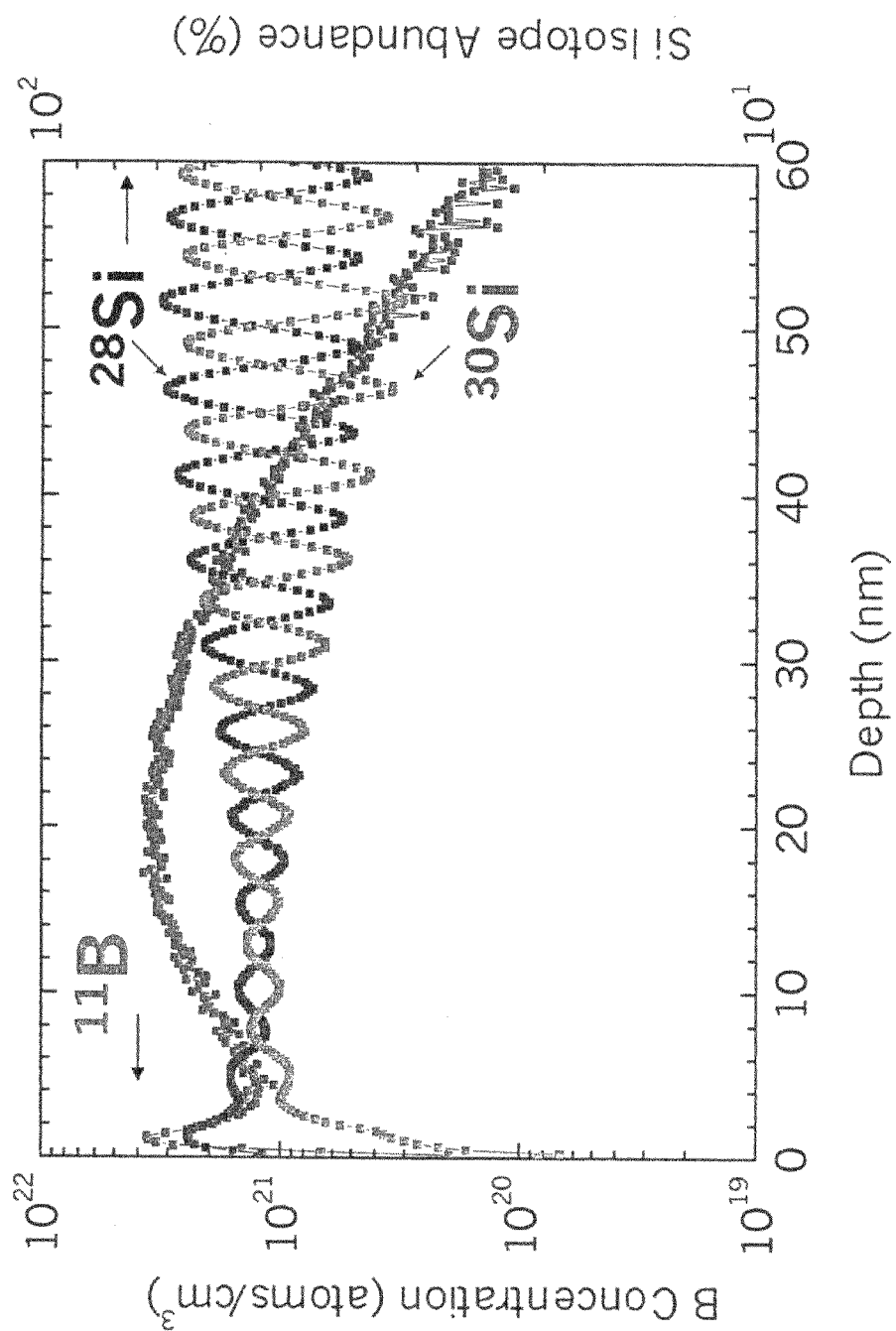
FIG. 12 is a view showing SIMS depth profiles of Si isotopes in the sample after implantation of B ions ($10^{16}$ cm$^{-2}$)

Referring to FIG. 12, there is presented a view showing SIMS depth profiles of Si isotopes in the sample after implantation of B ions ($10^{16}$ cm$^{-2}$). It can be seen that mixing is caused to a depth of 40 nm from the surface.

Also, in this case, when the simulation is performed as stated above to determine the fitting parameters k, c and d so that an experimental result is recreated more accurately, substrate damage by implantation of B ions can be simulated with high accuracy.

Consequently, in regard to various kinds of ions, values of the fitting parameters k, c and d for each dose are stored in a process simulator, whereby substrate damage by ion implantation can be simulated with high accuracy, for example.

Also, it is possible to quantitatively evaluate the change in mixing in the course of various types of thermal treatments to be executed after ion implantation, based on the changes in distributions of $^{28}Si$, $^{30}Si$ and the like.

Second Embodiment

Next, a method of evaluating mixing caused by ion implantation according to the second embodiment of the invention will be described with reference to FIG. 13. The basic arrangement thereof is exactly the same as that for the first embodiment, and therefore only critical points thereof will be described here.

Referring now to FIG. 13, there is presented a view for comparison of sample evaluation between SIMS and Raman scattering. Also, in this case, $^{28}Si_{20}/^{30}Si_{20}$ isotope superlattice samples were measured.

The Raman scattering depth profiles of isotopes in the lower portion of the drawing exhibit much sharper interfaces in comparison to SIMS depth profiles of isotopes in the upper portion of the drawing, which shows that little mixing of $^{28}Si$ and $^{30}Si$ is caused at an interface between $^{28}Si_{20}$ layer and $^{30}Si_{20}$ layer.

The Raman scattering depth profile of an isotope has been known to have a high accuracy (see Thin Solid Films, Vol. 508, p. 160, 2006, as required). In contrast, it is thought that the SIMS depth profile of an isotope reflects a knock-on effect on silicon atoms caused by irradiation of $Cs^+$ ions in a step of SIMS.

Therefore, when SIMS depth profiles of the isotopes are corrected so as to recreate Raman scattering depth profiles of isotopes before ion implantation, the influence by irradiation of $Cs^+$ ions at the step of SIMS can be eliminated. As a result, a simulation about substrate damage by ion implantation can be performed with high accuracy.

Third Embodiment

Next, a method of evaluating mixing caused by ion implantation according to the third embodiment of the invention will be described with reference to FIG. 14. The basic arrangement thereof is exactly the same as that for the first embodiment, and therefore only critical points thereof will be described here.

Figure 14:
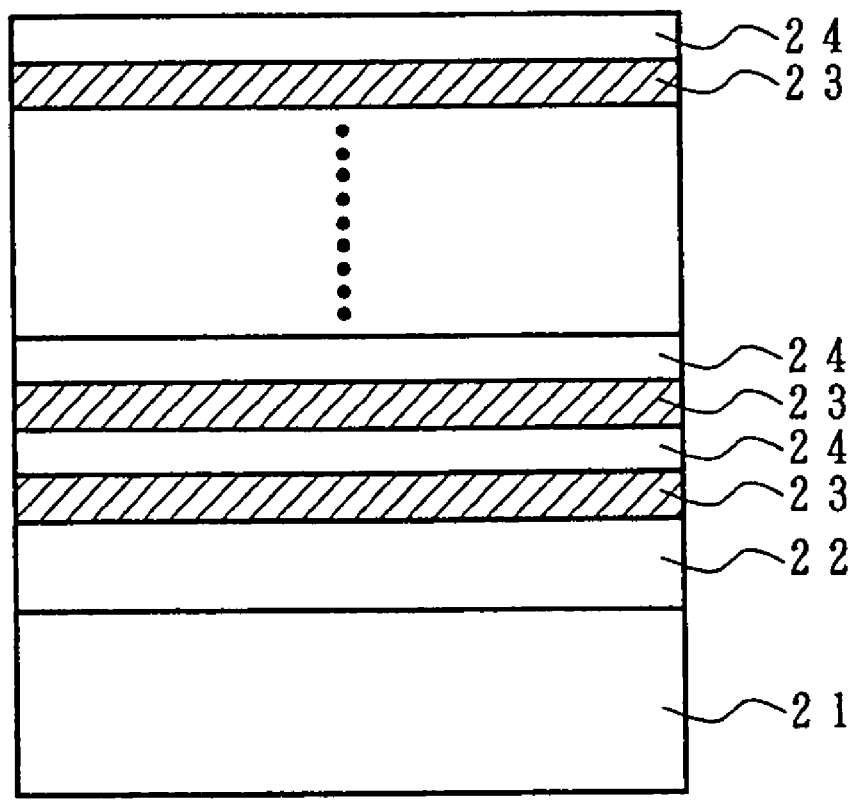
FIG. 14 is a schematic sectional view of a sample used in the method of evaluating mixing caused by ion implantation according to the third embodiment of the invention.

Referring to FIG. 14, there is presented a schematic sectional view of a sample used in the method of evaluating mixing caused by ion implantation according to the third embodiment of the invention. On a Si buffer layer 22 of a natural composition ratio on a monocrystalline Si substrate 21 having a natural composition ratio with its (001) plane made a top surface, $^{28}Si_{20}$ layers 23 each composed of twenty atomic layers and $Si_{20}$ layers 24 each composed of twenty atomic layers and having the natural composition ration are alternately stacked to e.g. fifteen cycles of the layers by means of molecular beam epitaxy.

In this case, the abundance of $^{30}Si$ in each layer is 0% approximately in $^{28}Si_{20}$ layer 23, and 3.1% in $Si_{20}$ layer 24. Therefore, the following procedure may be followed. That is, the change in $^{30}Si$ distribution is measured by means of SIMS, and the fitting parameters k, c and d are determined so that the result of the measurement is recreated by the simulation with high accuracy.

As stated above, according to the third embodiment of the invention, as a $^{28}Si_{20}/Si_{20}$ superlattice sample is used as a sample, purified gaseous raw material of $^{30}Si$ is not needed, which enables significant reduction in the manufacturing cost of samples. As a result, the cost for a process of collecting data to be stored in the process simulator can be cut down, and therefore the process simulator can be supplied at a low cost.

Fourth Embodiment

Next, a method of evaluating mixing during the time of ion machining according to the fourth embodiment of the invention will be described with reference to FIG. 15.

Referring to FIG. 15, there is presented a view of assistance in explaining the dependence of substrate damage on an ion species used for irradiation. The upper portion of the drawing shows the mixing effect in the case where a $^{28}Si_{20}/^{30}Si_{20}$ isotope superlattice sample, which is exactly the same as that used according to the first embodiment, is etched with $O_2^+$ ions at an acceleration energy of 5 keV. The lower portion of the drawing shows the mixing effect in the case where the sample is etched with $Cs^+$ ions at an acceleration energy of 5 keV.

As is clear from the difference in amplitude between the profiles shown in the drawing, the mixing effect caused by $O_2^+$ ions is larger than that owing to the mixing effect by $Cs^+$ ions. Also, in this case, the above-described simulation may be performed thereby to determine the fitting parameters k, c and d so as to recreate the result of measurement by SIMS with high accuracy.

Also, in this case, the abundance of $^{28}Si$ higher than that of $^{30}Si$ in each periodic structure is not ascribable to the mixing, and it can be inferred that such relation of the isotope abundances results from the step of normalization with respect to the Si buffer layer having the natural composition ratio.

When the dependence of substrate damage involved in such ion machining on the ion species is taken in the process simulator as the fitting parameters k, c and d, damage to a substrate by ion machining can be simulated with high accuracy.

Also, the comparison between the mixing effect caused by $Cs^+$ ions at an acceleration energy of 1 keV as shown in FIG. 3 and the mixing effect caused by $Cs^+$ ions at an acceleration energy of 5 keV as shown in the lower portion of FIG. 15 enables the acquisition of data concerning the dependence of substrate damage involved in ion machining on acceleration energies.

Therefore, when data on the dependence of substrate damage involved in ion machining on acceleration energies, i.e. the fitting parameters k, c and d for the respective acceleration energies, another ion mixing model, etc. are stored in the process simulator, it becomes possible to perform a process simulation with higher accuracy.

While the embodiments of the invention have been described above, the invention is not limited to the arrangements and conditions stated in the embodiments and various changes and modifications may be made. For example, as for the above-described embodiments, the number of atomic layers constituting each layer is set to twenty, however the invention is not limited to the twenty atomic layers, and a $^{28}Si_n/^{30}Si_n$ or $Si_n/^{30}Si_n$ isotope superlattice sample having an arbitrary number n of atomic layers may be used.

In order to evaluate a damage owing to a low acceleration energy with higher accuracy, for example, the sample may be arranged under the condition of n<20. To evaluate a damage owing to a higher acceleration energy with higher accuracy, the sample may be arranged under the condition of n>20.

In addition, as for the embodiments, attention has been directed toward $^{28}$Si and $^{30}$Si as isotopes, a combination of $^{28}$Si and $^{29}$Si or $^{29}$Si and $^{30}$Si may be used.

Further, with the first embodiment, the result of measurement of a sample after ion implantation, but before annealing has been shown, the details of the description are common to the sample which has undergone annealing. That is, the mixing condition and distribution of As after annealing are measured, and the fitting parameters are determined so as to recreate the results of the measurement faithfully as far as possible, whereby a process simulation can be performed with higher accuracy.

Still further, with the above embodiments, the invention has been described assuming that it is applied to a Si process. However, the invention is also applicable to a device using SiGe layers. In that case, only Si contained in each SiGe layer may be regarded as making up an isotope superlattice structure. Otherwise, germanium (Ge) contained in each SiGe layer may be also regarded as making up a superlattice structure with the isotopes.

Incidentally, it is desirable to use $^{70}$Ge and $^{76}$Ge for the purpose of increasing the accuracy of SIMS analysis because the isotope abundances of Ge are as follows.

$^{70}$Ge: 20.5%
$^{72}$Ge: 27.4%
$^{73}$Ge: 7.8%
$^{74}$Ge: 36.5%
$^{76}$Ge: 7.8%

Further, the embodiments can apply to processes for III-V compound semiconductors of GaAs, etc. An isotope superlattice sample configured of $(^{69}Ga^{75}As)_n/(^{71}Ga^{75}As)_n$ may be used because the abundances of gallium (Ga) and arsenic (As) are as follows.

$^{69}$Ga: 60.1%
$^{71}$Ga: 39.9%
$^{75}$As: 100%

For example, as for an InGaAs-based field effect-type semiconductor device, the characteristic values derived from evaluation by the above-described method of evaluating an ion irradiation effect, e.g. fitting parameters determined by evaluating standard deviations of recoils of Ga, Al and In atoms in the vicinity of a hetero interface owing to ion irradiation are taken in the device simulator. As a result, it becomes possible to quantitatively evaluate the change in mobility of a carrier, the change in barrier height, etc. owing to the mixing of constituent atoms of a substrate caused by ion etching, ion implantation, and a subsequent thermal treatment.

A typical example of application of the invention is a process simulation in a semiconductor process. However, except a semiconductor device, the invention is also applicable to process simulations concerning damages to electronic devices caused by ions including damage to a superconducting device owing to ion milling.

What is claimed is:

1. A method of evaluating an ion irradiation effect comprising:
  a first irradiation of a sample with a beam of ions, said sample being prepared by alternately and periodically stacking at least a first thin film layer and a second thin film layer, and being for evaluating the displacement of atoms therein through irradiation with a beam of ions; and
  evaluating an influence of the ions used for the irradiation on atoms making up the sample,
  wherein the first thin film layer and second thin film layer are comprised of a same chemical element or elements wherein the chemical element or elements of the first thin layer is primarily comprised of a different isotope or isotopes of the chemical element or elements than an isotope or isotopes of the chemical element or elements in the second thin film layer,
  wherein the step of ion irradiation is one of an ion implantation step and an ion etching step, and
  the influence of the ions used for the first irradiation on atoms making up the sample is evaluated by means of secondary ion mass spectrometry, which uses a second irradiation of the sample.

2. A process simulator in which characteristic values derived from evaluation according to the method of evaluating an ion irradiation effect of claim 1 are stored as parameters.

3. A device simulator in which characteristic values derived from evaluation according to the method of evaluating an ion irradiation effect of claim 1 are stored as parameters.

4. A method of evaluating an ion irradiation effect comprising:
  a first irradiation of a sample with a beam of ions, said sample being prepared by alternately stacking a first thin film layer and a second thin film layer, and being for evaluating the displacement of atoms therein through irradiation with a beam of ions; and
  evaluating the influence of the ions on atoms making up the sample,
  wherein of the thin film layers, the first thin film layer and second thin film layer are comprised of a same chemical element or elements wherein the chemical element or elements of the first thin layer is primarily comprised of a different isotope or isotopes of the chemical element or elements than an isotope or isotopes of the chemical element or elements in the second thin film layer,
  wherein the step of ion irradiation is one of an ion implantation step and an ion etching step, and
  evaluating an influence of the ions used for the first irradiation on atoms making up the sample by means of secondary ion mass spectrometry, which uses a second irradiation of the sample.

5. A process simulator in which characteristic values derived from evaluation according to the method of evaluating an ion irradiation effect of claim 4 are stored as parameters.

6. A device simulator in which characteristic values derived from evaluation according to the method of evaluating an ion irradiation effect of claim 4 are stored as parameters.

7. A method of evaluating an ion irradiation effect comprising:
  forming a sample of a first thin film layer and a second thin film layer, said sample being for evaluating the displacement of atoms therein through irradiation with a beam of ions;
  irradiating said sample with a first beam of ions;
  evaluating the influence of the ions on the atoms making up the sample;
  wherein of the thin film layers, the first thin film layer and second thin film layer are comprised of a same chemical element or elements wherein the chemical element or elements of the first thin layer is primarily comprised of a different isotope or isotopes of the chemical element or elements than an isotope or isotopes of the chemical element or elements in the second thin film layer, wherein the step of ion irradiation is one of an ion implantation step and an ion etching step, and evaluating an influence of the ions used for the irradiation on atoms making up the sample by means of secondary ion mass spectrometry, which uses a second irradiation of the sample.

8. A process simulator in which characteristic values derived from evaluation according to the method of evaluating an ion irradiation effect of claim 7 are stored as parameters.

9. A device simulator in which characteristic values derived from evaluation according to the method of evaluating an ion irradiation effect of claim 7 are stored as parameters.

* * * * *